United States Patent [19]

Boden

[11] 4,348,416
[45] * Sep. 7, 1982

[54] FLAVORING WITH 1-ETHOXY-1-ETHANOL ACETATE - ACETALDEHYDE MIXTURES

[75] Inventor: Richard M. Boden, Monmouth Beach, N.J.

[73] Assignee: International Flavors & Fragrances Inc., New York, N.Y.

[*] Notice: The portion of the term of this patent subsequent to Oct. 20, 1998, has been disclaimed.

[21] Appl. No.: 287,935

[22] Filed: Jul. 29, 1981

Related U.S. Application Data

[63] Continuation-in-part of Ser. No. 176,111, Aug. 7, 1980, Pat. No. 4,296,137.

[51] Int. Cl.$^3$ .................... A23L 1/226; A23L 1/235
[52] U.S. Cl. ........................ 426/3; 426/534; 426/96; 131/276; 252/522 R
[58] Field of Search ................ 426/3, 534, 96

[56] References Cited

U.S. PATENT DOCUMENTS 4,296,137 10/1981 Boden .................... 426/534

Primary Examiner—Joseph M. Golian
Attorney, Agent, or Firm—Arthur L. Liberman

[57] ABSTRACT

Described for use in foodstuffs, chewing gums, toothpastes, medicinal products flavor and aromas, smoking tobacco flavor and aroma and perfume, cologne and perfumed article aroma augmenting, modifying, enhancing and imparting compositions and as foodstuffs, chewing gums, toothpastes, medicinal products, tobacco, perfume and perfumed article and cologne aroma imparting materials are mixtures of 1-ethoxy-1-ethanol acetate having the structure:

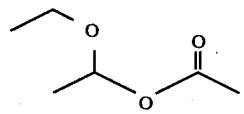

(also hereinafter referred to as "E") and acetaldehyde (also hereinafter referred to as "A"), the range of weight ratios, E:A being from 50:50 down to 5:95.

15 Claims, 2 Drawing Figures

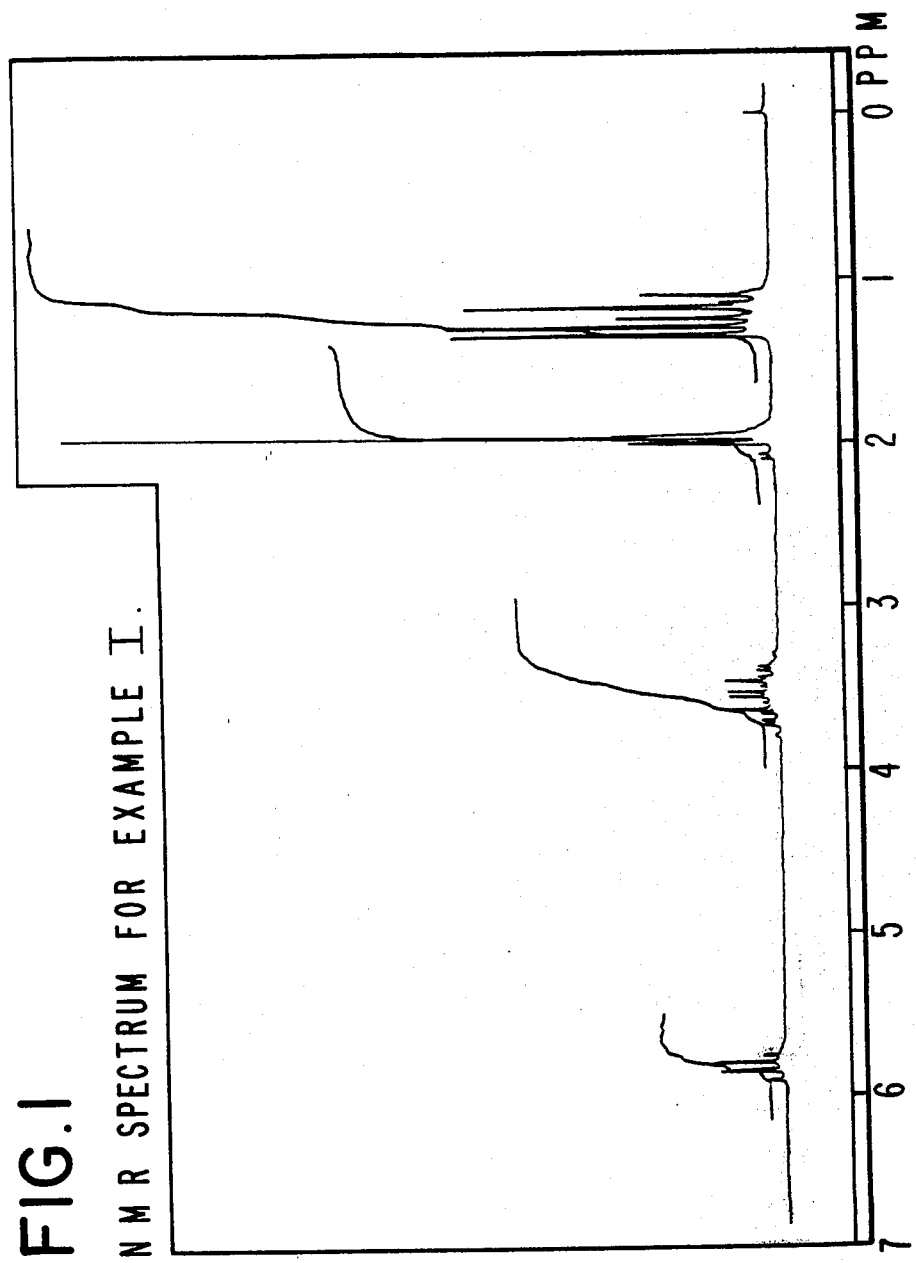

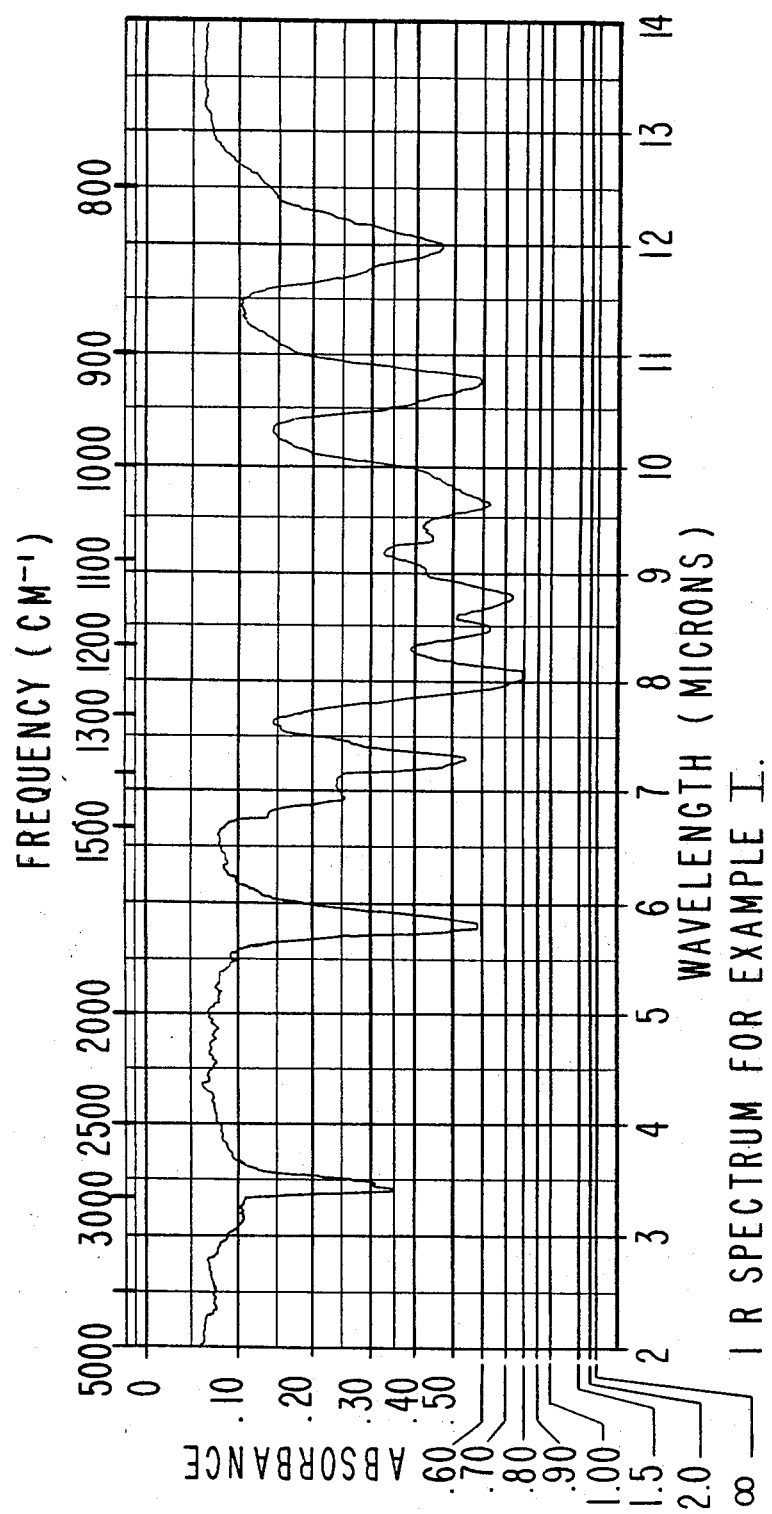

FLAVORING WITH 1-ETHOXY-1-ETHANOL ACETATE - ACETALDEHYDE MIXTURES

This application is a continuation-in-part of application for U.S. Letters Patent, Ser. No. 176,111 filed on Aug. 7, 1980, now U.S. Pat. No. 4,296,137 issued on Oct. 20, 1981.

BACKGROUND OF THE INVENTION

This invention relates to a novel method of fixing acetaldehydes by means of the formation of 1-ethoxy-1-ethanol acetate which acts as a generator responding to conditions of use in a food product to yield acetaldehyde. This invention also relates to the use of mixtures of 1-ethoxy-1-ethanol acetate having the structure:

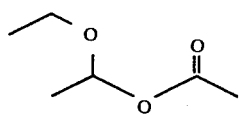

and acetaldehyde in flavors or taken alone or combined in carbohydrates, such as cyclic dextrins to generate acetaldehyde.

It is well known that acetaldehyde occurs in a wide variety of fresh and prepared foodstuffs, such as fruits, meat, dairy products, baked goods and vegetables. Acetaldehyde has been found particularly important in contributing to the flavor impact in "fresh" effect of certain foodstuffs especially of the citrus fruit and red berry types. As such, it is indispensable in compounding artificial flavors where the "fresh" effect is needed, plus, as early as 1921 acetaldehyde has been indicated to be useful in the formulation of a synthetic apple oil, as indicated in U.S. Pat. No. 1,366,541 issued on June 25, 1921 and as indicated in U.S. Pat. No. 1,436,290 issued on Nov. 21, 1922. In addition, acetaldehyde has been found to be important in contributing to the flavor impact of coffee flavor. Thus, U.S. Pat. No. 1,696,419 issued on Dec. 25, 1928 as well as United Kingdom Pat. No. 260,960 accepted on Feb. 22, 1928 disclose the utility of acetaldehyde in augmenting and enhancing the aroma and taste of coffee. Although it is also well known to fix acetaldehyde in the form of the diethyl acetal as is seen in U.S. Pat. No. 3,140,184, wherein the diethyl acetal of acetaldehyde and a beta-cyclic dextrin complex are added to a dry beverage mix to produce a pleasant tasting beverage having a characteristic flavor and odor of fresh oranges, the optimization of the rate of generation of acetaldehyde aroma in the citrus-tasting beverage has never quite been achieved. Thus, German Offenlegungsschrift No. 2,802,821, published on July 27, 1978 corresponding to United States Application for Letters Patent Ser. No. 761,183, filed on Jan. 21, 1977, discloses a number of acetaldehyde precursors including the acetaldehyde precursor having the structure:

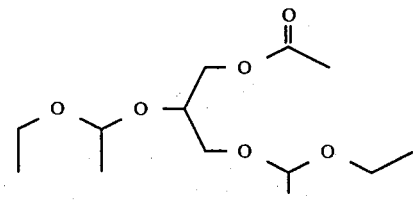

None of the acetaldehyde precursors; either those of German Offenlegungsschrift No. 2,802,821, including that having the structure:

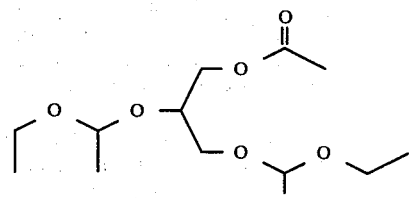

or those of U.S. Pat. No. 3,140,184, including that having the structure:

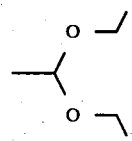

have as advantageous a flavor and aroma impact and have as advantageous a fragrance impact as the mixtures of 1-ethoxy-1-ethanol acetate having the structure:

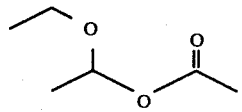

with acetaldehyde whether they are used as is, or whether they are combined with an absorbing solid such as an acyclic dextrin.

BRIEF DESCRIPTION OF THE DRAWINGS

FIG. 1 is the NMR spectrum for 1-ethoxy-1-ethanol acetate produced according to Example I.

FIG. 2 is the infra-red spectrum for 1-ethoxy-1-ethanol acetate produced according to Example I.

THE INVENTION

It has now been determined that mixtures of 1-ethoxy-1-ethanol acetate and acetaldehyde are capable of imparting a variety of flavors and fragrances to various consumable materials, and are also capable of augmenting or enhancing a variety of flavors and fragrances of various consumable materials.

Briefly, our invention contemplates augmenting or enhancing the flavors and/or fragrances of such consumable materials as perfumes, perfumed articles, colognes, foodstuffs, chewing gums, toothpastes, medicinal products and smoking tobaccos by adding thereto, a small but effective amount of mixtures of 1-ethoxy-1-ethanol acetate having the structure:

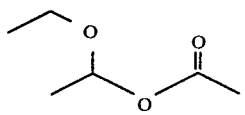

and acetaldehyde, the range of weight ratios of 1-ethoxy-1-ethanol acetate:acetaldehyde varying between 50 parts 1-ethoxy-1-ethanol acetate:50 parts acetaldehyde down to 5 parts 1-ethoxy-1-ethanol acetate:95 parts acetaldehyde.

The mixtures of 1-ethoxy-1-ethanol acetate and acetaldehyde of my invention augment or enhance fresh, fruity, somewhat acetaldehyde-like, propionaldehyde-like, acetic acid-like and ethereal-like aroma and flavor characteristics insofar as augmenting or enhancing the aroma or taste of foodstuffs, toothpastes, medicinal products and chewing gums.

The mixtures of 1-ethoxy-1-ethanol acetate and acetaldehyde of my invention also augment or enhance the sweet, fruity and winey aromas of perfumes, perfumed articles and colognes of my invention.

The mixtures of 1-ethoxy-1-ethanol acetate and acetaldehyde of my invention also augment or enhance the sweet, fruity, winey, fresh and berry characteristics of smoking tobacco, both prior to and on smoking, by imparting thereto a "life" and freshness. The stability advantage of mixtures of 1-ethoxy-1-ethanol acetate and acetaldehyde over acetaldehyde itself is quite profound, yet its ability to liberate the acetaldehyde nuance in smoking tobacco is unexpected, unobvious and advantageous.

The 1-ethoxy-1-ethanol acetate of my invention may be prepared according to processes well known in the prior art, for example, according to the reaction:

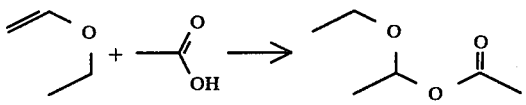

Such a process is more specifically pointed out in Example I, infra, as well as in the article by Topchieva and Stepanova Vestnik Moskov. Univ. Ser. II, 15, No. 3, 3–6 (1960) (abstracted in Chem Abstracts at Chem Abstracts 1961, Column 2469h (Vol. 55).

The 1-ethoxy-1-ethanol acetate of my invention can be obtained in pure form, or in substantially pure form by conventional purification techniques. Thus, the products can be purified and/or isolated by distillation, preparative chromatographic techniques (column chromatography and vapor phase chromatography) and the like. It has been found desirable to purify the 1-ethoxy-1-ethanol acetate of my invention by fractional distillation in vacuo.

When the mixtures of 1-ethoxy-1-ethanol acetate and acetaldehyde of my invention are used as food flavor adjuvants, the nature of the co-ingredients included with said mixtures of 1-ethoxy-1-ethanol acetate and acetaldehyde in formulating the product composition will also serve to alter, modify, augment or enhance the organoleptic characteristics of the ultimate foodstuff treated therewith.

As used herein in regard to flavors, the terms "alter", "modify" and augment in their various forms, mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks, and the like.

As used herein, the term "medicinal product" includes both solids and liquids which are ingestible, non-toxic materials which have medicinal value such as cough syrups, cough drops, aspirin and chewable medicinal tablets.

The term "chewing gum" is intended to mean a composition which comprises a substantially water insoluble, chewable plastic gum base such as chicle, or substitutes therefor, including jelutong, guttakay rubber or certain cosmetible natural or synthetic resins or waxes. Incorporated with the gum base in admixture therewith may be plasticizers or softening agents, e.g., glycerine, and a flavoring composition which incorporates the mixtures of 1-ethoxy-1-ethanol acetate and acetaldehyde of my invention, and, in addition, sweetening agents which may be sugars, including sucrose or dextrose and/or artificial sweeterners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumble material used is not caused to have unacceptable aroma and taste nuances. Such materials may in general be characterized as flavoring adjuvants or vehicles comprising, broadly, stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxy anisole), butylated hydroxytoluene (2,6-di-tertiary-butyl-4-methyl phenol), propyl gallate and the like, and sequestrants, e.g., citric acid.

Thickener compounds include carriers, binders, protective colloids, suspending agents, emulsifiers and the like, e.g. agar agar, carrageenan; cellulose and cellulose derivatives such as, carboxymethyl cellulose and methyl cellulose; natural and synthetic gums such as gum arabic, gum tragacanth; gelatin, proteinaceous materials; lipids, carbohydrates; starches, pectins, and emulsifiers, e.g., mono- and diglycerides of fatty acids, skim milk powder, hexoses, pentoses, disaccharides, e.g., sucrose, corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like, firming agents such as aluminum sodium sulfate, calcium chloride and calcium gluconate; texturizers, anticaking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids. e.g., acetic acid, formic acid, 2-hexenoic acid, benzoic acid, n-butyric acid, caproic acid, caprylic acid, cinnamic acid, isobutyric acid, isovaleric acid, alphamethylbutyric acid, propionic acid, valeric acid, 2-methyl-2-pentenoic acid and 2-methyl-3-pentenoic acid; ketones and aldehydes, e.g., 2-methyl-3-ketofuran, acetophenone, acetone, acetyl methyl carbinol, acrolein, n-butanal, crotonal, diacetyl, 2-methylbutanal, beta-beta-dimethyl acrolein, methyl n-amyl ketone, n-hexanal, 2-hexenal, isopentenal, hydrocinnamic aldehyde, cis-3-hexenal, 2-heptenal, nonyl aldehyde, 4-(p-hydroxyphenyl)-2-butanone, alpha-ionone, beta-ionone, 2-methyl-3-butanone, benzaldehyde, beta-damascone, alpha-damascone, beta-damascenone, acetophenone, 2-heptanone, o-hydroxy-acetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl-furfural, cinnamaldehyde, beta-cyclohomocitral, 2-pentanone, 2-pentenal and propanal, alcohols such as 1-butanol, benzyl alcohol, 1-broneol, trans-2-buten-1-ol, ethanol, geraniol, 1-hexanol, 2-heptanol, trans-2-hexenol-1, cis-3-hexenol-1-ol, 3-methyl-3-buten-1-ol, 1-pentenol, 1-penten-3-ol, p-hydroxyphenyl-2-ethanol, isoamyl alcohol, isofenchyl alcohol, phenyl-2-ethanol, alpha-terpineol, cis-terpinhydrate, eugenol, linalool, 2-heptanol, acetoin; esters such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate, and terpenyl acetate; hydrocarbons such as dimethyl naphthalene, dodecane, methyldiphenyl, methyl naphthalene, myrcene, naphthalene, octadecane, tetradecane, tetramethylnaphthalene, tridecane, trimethylnaphthalene, undecane, caryophyllene, alphaphellandrene, beta-phellandrene, p-cymene 1-alpha-pinene, beta-pinene, dihydrocarveol; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils such as jasmine absolute, cassia oil, cinnamon bark oil, black pepper oleoresin, oil of black pepper, rose absolute, orris absolute, oil of cubeb, oil of coriander, oil of pimento leaf, oil of patchouli, oil of nutmeg, lemon essential oil, safran oil, Bulgarian rose, capsicum, yara yara and vanilla; lactones such as γ-nonalactone; sulfides, e.g., methyl sulfide and other materials such as maltol, and acetals (e.g., 1,1-diethoxyethane, 1,1-dimethyloxyethane and dimethoxymethane), piperine, chavicine, and piperdine.

The specific flavoring adjuvant selected for use may be either solid or liquid depending upon the desired physical form of the ultimate product, i.e. foodstuff, whether simulated or natural, and should, in any event, (i) be organoleptically compatible with the mixtures of 1-ethoxy-1-ethanol acetate and acetaldehyde of my invention by not covering or spoiling the organoleptic properties (aroma and/or taste) thereof; (ii) be non-reactive with the mixtures of 1-ethoxy-1-ethanol acetate and acetaldehyde of my invention and (iii) be capable of providing an environment in which the mixtures of 1-ethoxy-1-ethanol acetate and acetaldehyde can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contra-distinction, in the preparation of solid products, e.g., simulated foodstuffs, ingredients capable of providing normally solid compositions should be selected such as various cellulose derivatives.

As will be appreciated by those skilled in the art, the amount of mixture of 1-ethoxy-1-ethanol acetate and acetaldehyde employed in a particular instance can vary over a relatively wide range, depending upon the desired organoleptic effects to be achieved. Thus, correspondingly greater amounts would be necessary in those instances wherein the ultimate food composition to be flavored (e.g., with a fresh, fruity flavor) is relatively bland to the taste, whereas relatively minor quantities may suffice for purposes of enhancing the composition merely deficient in natural flavor or aroma. The primary requirement is that the amount selected be effective, i.e., sufficient to alter, modify or enhance the organoleptic characteristics of the parent composition, whether foodstuff per se, chewing per se, medicinal product per se, toothpaste per se or flavoring composition.

The use of insufficient quantities of mixture of 1-ethoxy-1-ethanol acetate and acetaldehyde will, of course, substantially vitiate any possibility of obtaining the desired results while excess quantities prove needlessly costly and in extreme cases may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of mixture of 1-ethoxy-1-ethanol acetate and acetaldehyde ranging from a small but effective amount, e.g., 0.05 parts per million up to about 500 parts per million based on total composition, are suitable. Concentrations in excess of the maximum quantity stated are not normally recommended since they fail to provide commensurate enhancement of organoleptic properties. In those instances wherein the mixtures of 1-ethoxy-1-ethanol acetate and acetaldehyde is added to the foodstuffs as an integral component of a flavoring composition, it is of course, essential that the total quantity of flavoring composition employed be sufficient to yield an effective mixture of 1-ethoxy-1-ethanol acetate/acetaldehyde concentration in the foodstuff product.

Food flavoring compositions prepared in accordance with the present invention preferable contain the mixture of 1-ethoxy-1-ethanol acetate and acetaldehyde in concentrations ranging from about 0.025% up to about 15% by weight based on the total weight of the flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the mixture of 1-ethoxy-1-ethanol acetate and acetaldehyde with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix, are obtained by mixing the dried solid components, e.g., starch, sugar and the like, and mixture of 1-ethoxy-1-ethanol acetate and acetaldehyde in a dry blender until the requisite degree of uniformity is achieved.

It is presently preferred to combine with the mixture of 1-ethoxy-1-ethanol acetate and acetaldehyde of my invention, the following adjuvants:

Natural Orange Oil; Ethyl Acetate; Ethyl Butyrate, n-Propanol; Trans-2-hexenal; Oil of Cubeb; Phellandrene; beta-Phellandrene; Oil of Coriander; Oil of Pimento Leaf, Oil of Patchouli; Natural Lemon Oil; Alpha-Terpineol; Citral; Carvone; Terpinolene; Alpha-Terpinene; Diphenyl; Alpha-Fenchyl Alcohol; Cineole; Limonene; Linalool; Geranyl Acetate; Nootkatone; Neryl Acetate; Heliotropin; Maltol; Vanillin; Ethyl Maltol; Ethyl Vanillin; Anisaldehyde; Alpha Pinene; Beta-Pinene; Beta-Caryophyllene; Dihydrocarveol; Piperonal; Piperine; Chavicine; Piperidine; Oil of Black Pepper, Black Pepper Oleoresen; Capsicum; Oil of Nutmeg; Cardamom Oil; Clove Oil; Spearmint Oil; Oil of Peppermint; and $C_{10}$-Terpinyl Ethers as described in application for U.S. patent Ser. No. 872,937 filed on Jan. 27, 1978, now U.S. Pat. No. 4,131,687, issued on Dec. 26, 1978 (such as fenchyl ethyl ethers).

In accordance with an additional aspect of the present invention, novel 1-ethoxy-1-ethanol acetate-acetaldehyde mixture containing flavoring compositions (hereinafter referred to as E-A mixture containing compositions) capable of retaining at least 7% by weight of the E-A mixture stably over a long period of time are obtained according to the present invention by a freeze-drying method which comprises subliming water vapor from ice crystals by means of applying a vacuum to a frozen mixture comprising (a) from 6 to 1 parts water; (b) from about 4 to 2 parts of an ingestibly acceptable, preferably cold water soluble, non-hygroscopic carrier comprising a carbohydrate and (c) from 2 to 1 parts of E-A mixture.

The compositions produced in accordance with the present invention contain levels of E-A mixture as low as about 7% and as high as about 20% by weight; preferably about 10% by weight based on the total weight of E-A mixture, non-hygroscopic carbohydrate carrier and water, such quantities being stably retained in the product composition despite exposure of the composition to the atmosphere for periods of one month and longer.

The initial aqueous mixture of E-A mixture and carrier is preferably prepared at temperatures on the order of 30° to 50° F. and thus, the carrier material employed should be substantially if not completely water soluble within this temperature range. Admixing the materials, as by solubilizing, slurrying, or making a paste thereof, within this temperature range is desirable by reason of the volatility of the acetaldehyde. Where elevated temperatures are necessary to more fully incorporate the carrier in the aqueous medium, the mixture may be prepared by admixing the carrier in water by dissolving or slurrying, at the necessary elevated temperature, e.g., 175°–212° F., cooling the mixture paste thus formed to a temperature of from 30° to 50° F. and then adding the E-A mixture. Alternatively, the E-A mixture may be added by refluxing; and thus returning same into the aqueous carrier mixture while the latter is cooling. Yet another method involves mixing the carrier, E-A mixture and water in a reflux tank at a temperature from about 130° to 180° F. The relative quantities of the respective components employed in forming the aqueous mixture range from about 2 to 4 parts carrier, from about 2 to 1 parts E-A mixture, and from 1 to 6 parts water. In accordance with particularly preferred practice, the carrier is added to the aqueous medium in amounts sufficient to form a supersaturated solution, this being achieved by the addition of about 25–45% by weight of carrier to the aqueous medium.

The use of supersaturating quantities of carrier is particularly advantageous since the E-A mixture, in enhancing the solubility of the carrier in water, effectively increases the quantity of carrier available for "entrapping" or "locking in" acetaldehyde in the since of rendering the entrapped acetaldehyde stable.

Non-hygroscopic, preferably cold water soluble, carbohydrate matrix materials suitable for use in the present invention include, for example, the hydrolyzed cereal solids product manufactured by Corn Products Industrial, Division Corn Products Company, and available under the trade name designation MOR-REX; a liquid dextrine commercially available from the Clinton Corn Co. under the trade name designation LIQUI-DEX and containing about 73% solids, the remainder comprising moisture, the solids comprising essentially a mixture of saccharides, e.g., monosaccharides (dextrose), disaccharides (maltose), the latter ingredients being present in trace quantities, trisaccharides, tetrasaccharides, pentasaccharides, hexasaccharides, heptasaccharides, octasaccharides with higher saccharides constituting about 46% by weight on a dry basis; a hydrolyzed cereal solids mixture available commercially from the Grain Processing Corporation under the trade name designation MALTRIN-10 and comprising a mixture containing about 1% dextrose, 77.0% hexasaccharide, with the remainder being constituted by varying amounts of di-, tri-, tetra-, and penta-saccharides; a food-grade dextrin manufactured by the National Starch and Chemical Corporation and available commercially under the trade name designation CAPSUL; mixtures of reducing and non-reducing sugars obtained by means of controlled enzymatic hydrolysis of starch available in grade designations, "T", "A23" and "67", materials of this type being manufactured by W. A. Scholten's Chemische Fabricken, N.V. and available commercially under the trade name designation MALTO-DEXTRINE.

The aforedescribed materials and particularly the hydrolyzed cereal solids are beneficially adapted for use in the practice of the present invention since in addition to having the requisite degree of non-hygroscopicity they are, for the most part, bland to the taste, i.e., present no "starchy" flavor, exhibit no tendency to mask flavor even at high solids levels, do not cake on standing, yield clear as to be distinguished from "milky" solutions by virtue of their excellent "cold" water solubility, are outstanding bulking agents and, therefore, highly effective for carrying sweeteners and flavoring agents, are superior from a bodying standpoint and thus, from an aesthetic standpoint, have improved mouthfeel and offer greater viscosity. Other carbohydrate materials which may be employed herein include modified starches, modified cellulose, gelatins, simple sugars, sucrose, glucose, lactose, gums, gum arabic, a mixture (50/50) of ethylcellulose and methylcellulose, and the like.

It will further be understood that the aforedescribed materials may be employed either singly or in admixtures comprising two or more thereof. In this manner, the formulator is provided with effective means whereby to exploit the beneficial characteristics of each of a plurality of carbohydrate matrix materials in a given instance and thus comprises a particularly effective mode of proceeding. In addition, the use of mixtures entails the highly significant advantage that the carbohydrate matrix may be "tailored" to the requirements imposed upon the formulator in a given instance.

It is recognized, of course, that in certain instances, the carbohydrate material as supplied for use may contain very minor quantities of, for example, iron, ash, or the like. Accordingly, the terminology carbohydrate carrier as used in the context of the present invention is to be accorded a significance consistent therewith.

The aqueous mixture of carrier, E-A mixture and water prepared as described hereinbefore, may be converted to a completely frozen state according to procedures well known in the art. The temperature employed for freezing should be substantially below the eutectic point of the aqueous, E-A mixture system which will usually be within the range of $-50°$ F. to $-10°$ F. The term, "eutectic point" as used herein means the lowest temperature at which a specific mixture of E-A mixture, carrier and water solidifies.

In addition, the particular freezing method selected will depend upon the physical form desired in the frozen specimen, i.e., in the form of a particulate solid or as a solid mass, e.g., slab or the like. To produce the frozen material in the form of particles, the aqueous mixture of carrier and E-A mixture may be frozen in the form of droplets by dropwise addition of such mixture into liquid nitrogen. In such instances, the particle size of the frozen material varies from approximately $\frac{1}{4}$ to $\frac{1}{2}$ cm.

Alternatively, continuous freezing techniques such as spray-freezing and continuous belt freezing may be employed as well as the more commonly employed method of batch freezing of the aqueous mixture in shallow metal trays, e.g., stainless steel or aluminum. According to the latter, the aqueous mixture is merely poured into the trays to a maximum depth of about $\frac{1}{2}$ inch and preferably about $\frac{1}{4}$ inch. Depths in excess of $\frac{1}{2}$ inch are not normally recommended since the time required for freezing the mixture is correspondingly prolonged. The trays containing the aqueous mixture may thereafter be placed as such in a conventional freezing chamber for carrying out the freeze-drying operation.

In those instances wherein the mixture is frozen in the form of a continuous solid mass such as a slab, it may thereafter be granulated, if desired, to form smaller particles by any suitable trituration means. However, the size-reduction operation must, of course, be carried out under conditions which insure against any possibility of melting the frozen particles; accordingly, the equipment as well as environment must be maintained at a temperature below the eutectic temperature of the frozen mass. The low temperature freezing treatment should be carried out to a point at which complete freezing of the aqueous mixture is achieved. Thus, it is critical in the practice of the present invention that little or no water be present during the freeze-drying operation since this tends to vitiate the efficiency of the water removal treatment which must be effected solely or at least substantially by sublimation in order to minimize acetaldehyde or E-A mixture loss. Without intending to be bound by any theory, it is postulated that the frozen ice phase is actually in equilibrium with a concentrated liquid phase, the water concentration of the liquid phase being a function of the ice temperature. Thus, at low ice temperature and thus low water concentrations in the liquid phase, the diffusion coefficient of the acetaldehyde, the 1-ethoxy-1-ethanol acetate and the E-A mixture in the liquid concentrate between the ice crystals is relatively low compared to that of water, this condition being promotive of E-A mixture retention.

In accordance with the present invention, freeze-drying of the frozen mass obtained as hereinbefore explained is carried out under vaccum with heat being supplied at a rate sufficient to remove water by sublimation. It is critical, of course, that the quantity of heat supplied correspond to that amount necessary to expedite sublimation of ice during the freeze-drying process; however, at the same time, such quantity of heat should not be such as to raise the temperature of the frozen material above its eutectic point.

The foregoing can be accomplished, for example, by maintaining the frozen composition at a temperature within the range of $-70°$ to $-10°$ F. and preferably slightly below the eutectic temperature of the mixture and at an absolute pressure of less than about 1000 microns of mercury with a range of 100 to 300 microns of mercury being preferred. The requisite rate of heat input can be accomplished by employing a shelf temperature within the range of $-30°$ F. to $+100°$ F. During the initial phase of the freeze-drying process, removal of the water from the ice crystals by sublimation results from the direct application of heat to the ice crystal, such process being endothermic in that heat input is required. Thus, the heat must be introduced at the drying boundary to support the sublimation of water vapor. As the freeze-drying process proceeds, an outer shell or layer of dried material forms, such layer representing the primary obstacle to heat transfer. Accordingly, drying in this phase of the process occurs for the most part by transfer of water vapor from the vicinity of the ice crystal at the drying boundary through the outer shell or layer of dried material to the outer surface of the frozen specimen. As will be noted, there is a tendency for the temperature in the dried outer layer to rise; such temperature rise is not absolutely proscribed by the present invention provided no significant loss of acetaldehyde or E-A mixture or 1-ethoxy-1-ethanol acetate occurs. This, of course, can be determined empirically by merely conducting a flavor retention study involving a plot of time versus temperature in order to determine the locus of limiting values demarking the incipient stages of significant flavor loss. In any event, accurate measurement of the temperature profile in the dried portion of the E-A mixture-containing composition can be effected with reasonable accuracy by placing a thermocouple at or slightly below the surface of the large particle of frozen composition.

The heat energy necessary to effect removal of water from the frozen mass by sublimation may be supplied by any suitable heating device conventionally employed in the art for such purposes including, for example, radiant heaters, conduction heating plates and the like. In any event, the rate of heat input should be sufficient to facilitate the desired sublimation rate without causing the temperature of the frozen mass to rise to its eutectic point since this would give rise to undesired melting and concomitant loss of acetaldehyde, 1-ethoxy-1-ethanol acetate or E-A mixture. The use of the shelf temperatures hereinbefore defined minimizes any possibility of melting. In some instances it is found advantageous, toward the end of the constant rate drying period, to employ dielectric heating means in order to confine the predominant part of the heat energy absorption to the inner ice portion.

The condenser means employed in the vacuum chamber should be maintained at a lower temperature than the frozen E-A mixture-containing mass since it is necessary that the vapor pressure of the frozen mass exceed the vapor pressure of the condenser so that the sublimed water vapor migrates from the frozen material to the condenser.

The pressure maintained within the vacuum freeze-drying chamber should be less than about 1000 microns of mercury and more preferably, within the range of 100 to 300 microns of mercury since any rise in pressure is accompanied by a corresponding increase in the equilibrium temperature; should the increased temperature exceed the eutectic temperature of the frozen mass, the latter will melt giving rise to the formation of liquid water, evaporation of the latter unavoidably involving significant loss of acetaldehyde, 1-ethoxy-1-ethanol acetate or E-A mixture as previously explained.

The "vacuum drying" or "desorption" cycle of the freeze-drying process corresponds to that portion of the process wherein all the water ice crystals have been sublimed and the eutectic mixture of carrier, E-A mixture and water is dried to the desired stable moisture content. Actually this stage of the drying cycle need not be strictly sublimation since some evaporation of water from the liquid state may occur without melting the frozen extract. In accordance with preferred practice, the freeze-drying process is carried out so as to provide a final E-A mixture-carrier composition having a moisture content within the range of 0.1% to 1.5% by weight of total composition.

Apparatus suitable for use in carrying out freeze-drying in accordance with the present invention is disclosed, for example, in Catson, et al., "Freeze Drying of Foodstuffs" (Columbine Press, Manchester, Entland, 1963, Chapter 4), this article describing a contact plate system. Other apparatus suitable for use herein is described in U.S. Pat. Nos. 2,616,604 and 2,853,796. The apparatus described in U.S. Pat. No. 2,616,604 is advantageously adapted for the freeze-drying of a mass provided in the form of small frozen particles of relatively uniform size. By way of contrast, the apparatus described in U.S. Pat. No. 2,853,796 is specifically adapted for the freeze-drying of a frozen sheet of specimen by sublimation. However, it will be understood that the specific nature of the apparatus employed is not a particularly critical factor in the practice of the present invention provided such apparatus be equipped to enable to removal by sublimation of water from the freeze-dried mass, whether the mass be provided in the form of a particulate solid or continuous solid mass.

In general, such apparatus should include as essential features, means to accommodate the frozen solution, whether in particulate or solid form, means to provide the necessary depressed temperatures, means to supply heat to the frozen mass at a rate sufficient to enable removal of water by sublimation, and means to remove and condense the sublimed vapors.

The freeze-dried compositions produced in accordance with the present invention may be utilized per se as flavoring compositions to simulate a wide variety of organoleptic factors whereby to evoke a predetermined taste response on the part of the consumer. As previously indicated herein, such compositions are particularly advantageously adapted for use in producing fruit-type flavors, e.g., those commonly found in a wide variety of beverages, candies, dessert foods, and the like. Moreover, in view of their exceptional moisture-stability under varying conditions, they may be readily employed in product compositions which would in all probability, as a result of repetitive use, contact humid environments. Thus, in the formulation of fruit flavors, the freeze-dried composition may be combined for example, with one or more additional flavorants, either natural or synthetic, citric acid, dextrose, sucrose and the like. Thus, gelatin jelly desserts may be prepared by combining the E-A mixture composition with a major quantity of sugar (i.e., on the order of 75 to 85 parts by weight) gelatin, citric acid, trisodium citrate and suitable fruit flavorants and colorants as desired. Low-calorie gelatin desserts may be prepared by combining the E-A mixture composition with a major quantity of gelatin, adipic acid, mono- and disodium phosphate, saccharin, one or more additional fruit flavorants, colorants and the like. In addition, low-calorie beverages may be prepared by combining the E-A mixture compositions with citric acid, mannitol, trisodium citrate, saccharin, tricalcium phosphate and one or more additional fruity flavorants, fruit colorants and the like.

In addition, the freeze-dried E-A mixture composition may be employed for purposes of enhancing one or more of the various flavor notes naturally present in meats and vegetables. In any event, the nature of the co-ingredients included with the freeze-dried composition will, of course, depend primarily upon the ultimate use contemplated, i.e., a foodstuff per se or alternatively, as a flavoring composition adapted to be added to a foodstuff at some subsequent point of time.

Substances suitable for use herein as co-ingredients or flavoring adjuvants are well known in the art for such use being extensively described in the relevant literature. Apart from the requirement that any such material be "ingestibly" acceptable and this non-toxic or otherwise non-deleterious, nothing particularly critical resides in the selection thereof. Accordingly, such materials, which may in general be characterized as flavoring adjuvants or vehicles comprise broadly, stabilizers, thickeners, surface agents, conditioners, flavorants and flavor intensifiers.

The specific flavoring adjuvant selected for use may be either solid or liquid, depending upon the desired physical form of the ultimate product, i.e., foodstuff whether simulated or natural, and should, in any event, be capable of providing an environment in which the freeze-dried E-A mixture-containing composition can be readily dispersed or admixed to provide a homogeneous medium. In addition, selection of one or more flavoring adjuvants as well as the quantity used thereof will depend upon the precise organoleptic character desired in the finished product; thus, in the case of the flavoring compositions, the ingredient selection will vary in accordance with the foodstuff to which the flavor and aroma are to be imparted. In contradistinction, in the preparation of solid products, e.g., simulated foodstuffs, ingredients capable of providing normally solid compositions should be selected.

As will be appreciated by those skilled in the art, the amount of freeze-dried E-A mixture-containing composition employed in a particular instance can vary over a relatively wide range whereby to achieve desired organoleptic effects having reference to the nature of the product. Thus, correspondingly greater amounts would be necessary in those instances wherein the ultimate food composition to be flavored is relatively bland to the taste, whereas relatively minor quantities may suffice for purposes of enhancing a composition merely deficient in natural flavor or aroma. Thus, the primary requirement is that the amount selected be effective, i.e., sufficient to alter the organoleptic characteristics of the parent composition. Thus, the use of insufficient quantities of the E-A mixture-containing composition will, of course, substantially vitiate any possibility of obtaining the desired results while excess quantities prove needlessly costly and in extreme case, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it is found that the freeze-dried composition should be employed in amounts sufficient to yield a quantity of E-A mixture within the range of from about 1 to 500 ppm based on total parts by weight of composition. Concentrations in excess of the maximum quantities stated are not normally recommended since they fail to provide commensurate enhancement of organoleptic properties.

The E-A mixture-containing flavoring composition may be further modified by addition of appropriate ingredients to provide yet further flavoring composition; in such instances, it is preferable that the freeze-dried composition be present in the mixture in amounts sufficient to yield an E-A mixture concentration within the range of from 0.001% to about 13% by weight based on the total weight of said flavoring composition.

The compositions described herein can be prepared according to conventional techniques well known in the art for such purposes. Thus, liquid products can be formulated by merely admixing the involved ingredients within the proportions stated in a suitable blender to obtain the desired consistency, homogeneity of dispersion, etc. Alternatively, the freeze-dried composition may be combined with additional ingredients to provide a particulate solid product by admixing the freeze-dried composition with, for example gum arabic, gum tragacanth, carrageenan and the like and, thereafter, spray-drying the resultant mixture whereby to obtain the particulate solid product. If it is desired to further combine the freeze-dried composition in the form of a powder flavor mix, this can be accomplished by mixing the dried solid components and freeze-dried composition in a dry blender until the requisite degree of uniformity is achieved.

The mixtures of 1-ethoxy-1-ethanol acetate and acetaldehyde of my invention, can be used to contribute fresh, fruity, acetaldehyde-like aromas to perfumes, perfumed articles and colognes. As olfactory agents, the mixtures of 1-ethoxy-1-ethanol acetate and acetaldehyde of my invention can be formulated into, or used as components of a "perfume composition" or can be used as components of a "perfumed article" (e.g., solid or liquid, anionic, cationic, nonionic or zwitterionic, detergents, fabric softeners, fabric softener articles or hair conditioners, or the like) or the perfume composition may be added to perfume, perfumed articles or cologne.

The term "perfume composition" is used herein to mean a mixture of organic compounds, including for example, alcohols, aldehydes, other than the acetaldehyde of my invention, ketones, nitriles, ethers, lactones, acetals, hemiacetals, ester acetals, other than the 1-ethoxy-1-ethanol acetate of my invention, natural essential oils, synthetic essential oils, and frequently, hydrocarbons, which are admixed so that the combined odors of the individual components produce a pleasant, or desired fragrance, e.g., a lemon fragrance. Such perfume compositions usually contain: (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) top notes which are usually low-boiling, fresh-smelling materials.

In perfume compositions, the individual component will contribute its particular olfactory characteristics, but the overall effect of the perfume composition will be the sum of the effects of each of the ingredients. Thus, the individual compounds of this invention, or mixtures thereof, can be used to alter the aroma characteristics of a perfume composition, for example, by highlighting or moderating the olfactory reaction contributed by another ingredient in the composition.

The amount of the mixtures of 1-ethoxy-1-ethanol acetate and acetaldehyde of this invention which will be effective in perfume compositions depends upon many factors, including the other ingredients, their amounts and the effects which are desired. It has been found that perfume compositions containing as little as 0.5% of the mixture of 1-ethoxy-1-ethanol acetate and acetaldehyde of this invention, or even less, can be used to impart an interesting, fresh, fruity, blueberry-like, acetaldehyde-like aroma to soaps, liquid and solid cationic, nonionic, anionic and zwitterionic detergents, cosmetics, powders, liquid and solid fabric softeners, dryer-added fabric softener articles, optical brightener compositions and other products. The amount employed can range up to 50% or higher and will depend on considerations of cost, nature of the end product and the effect desired on the finished product and particular fragrance sought. Thus, in summary, the range of mixture of 1-ethoxy-1-ethanol acetate and acetaldehyde in perfume compositions may range from 0.5% up to 50%.

The mixtures of 1-ethoxy-1-ethanol acetate and acetaldehyde of this invention can be used alone or in a perfume composition as an olfactory component in detergents and soaps, space odorants and deodorants; perfumes; colognes, toilet waters; bath salts; hair preparations such as lacquers, brilliantines, pomades and shampoos; cosmetic preparations such as creams, deodorants, hand lotions and sun screens; powders such as talcs, dusting powders, face powder and the like. When used as an olfactory component of a perfumed article, such as a solid or liquid anionic, cationic, nonionic or zwitterionic detergent, as little as 0.01% of the mixtures of 1-ethoxy-1-ethanol acetate and acetaldehyde will suffice to impart an interesting, fresh, fruity, blueberry-like, acetaldehyde-like aroma. Generally no more than 1.0% is required. Thus, the range of mixture of 1-ethoxy-1-ethanol acetate and acetaldehyde in perfumed articles will vary from 0.01% up to 1.0%.

In addition, the perfume composition containing the mixtures of 1-ethoxy-1-ethanol acetate and acetaldehyde of my invention can contain a vehicle or carrier for the mixture of 1-ethoxy-1-ethanol acetate and acetaldehyde, alone or with other ingredients. The vehicle can be a liquid such as an alcohol, such as ethanol, a glycol such as propylene glycol, or the like. The carrier can be an absorbent solid such as a gum or components for encapsulating the composition such as gelatin, which can be used to form a capsule wall surrounding the perfume oil as by means of coacervation.

An additional aspect of my invention provides an organoleptically improved smoking tobacco product and additives therefor including methods of making the same which overcome problems heretofore encountered in the creation or enhancement of specific desired sweet, fruity, winey, fresh berry-like notes. Such notes, both prior to and on smoking, in both the main stream and the side stream, may now be readily controlled and maintained at the desired uniform level regardless of variations in the tobacco components of the blend; or the nature of the filter used in conjunction with the smoking tobacco article.

This invention further provides improved tobacco additives and additives for materials used in the fabrication of tobacco articles (particularly smoking tobacco articles) and methods whereby desirable sweet, fruity, winey, fresh berry-like notes may be imparted to smoking tobacco products and may be readily varied and controlled to produce the desired uniform flavoring characteristics.

In carrying out this aspect of my invention, I add to smoking tobacco materials or a suitable substitute therefor (e.g., dried lettuce leaves) an aroma and flavor additive containing as an active ingredient, the mixtures of 1-ethoxy-1-ethanol acetate and acetaldehyde of my invention.

In addition to the mixtures of 1-ethoxy-1-ethanol acetate and acetaldehyde of my invention, other flavoring and aroma additives may be added to the smoking tobacco material or substitute therefor either separately or in admixture with the mixtures of 1-ethoxy-1-ethanol acetate and acetaldehyde:

| I. Synthetic Materials |
|---|
| Beta-methyl cinnamaldehyde; |
| Eugenol; |
| Dipentene; |
| β-Damascenone; |
| Maltol; |
| Ethyl maltol; |
| Delta-undecalactone; |
| Delta-decalactone; |
| Benzaldehyde; |
| Amyl acetate; |
| Ethyl butyrate; |
| Ethyl valerate; |
| Ethyl acetate; |
| 2-Hexen-1-ol; |
| 2-Methyl-5-isopropyl-1,3-nonadiene-8-one; |
| 2-Methyl-5-isopropylacetophenone; |
| 2-Hydroxy-2,5,5,8α-tetramethyl-1-(2-hydroxyethyl)-decahydronaphthalene; |
| Dodecahydro-3α,6,6,9α-tetramethylnaphtho(2,1-β)-furan; |
| 4-Hydroxyhexenoic acid, gamma-lactone; |
| Polyisoprenoid hydrocarbons defined in Example V of U.S. Pat. No. 3,589,372 issued on June 29, 1971 |

| II. Natural Oils |
|---|
| Celery seed oil; |
| Coffee extract; |
| Bergamot oil; |
| Cocoa extract; |
| Nutmeg oil; |
| Origanum oil; |

An aroma and flavoring concentrate containing the mixtures of 1-ethoxy-1-ethanol acetate and acetaldehyde of my invention and, if desired, one or more of the above indicated additional flavoring additives may be added to the smoking tobacco material, to the filter or the leaf or paper wrapper or to a filter which is part of the smoking article. The smoking tobacco material may be shredded, cured, cased and blended tobacco material or tobacco substitutes (e.g., dried lettuce leaves) or mixtures thereof. The proportions of flavoring additives may be varied in accordance with taste, but insofar as enhancement of the imparting of sweet, fruity, winey, fresh-berry-like notes prior to and on smoking, in both the main stream and the side stream, I have found that satisfactory results are obtained if the proportion by weight of the sum total of 1-ethoxy-1-ethanol acetate to smoking tobacco material is between 50 parts per million and 1500 parts per million (0.005%–0.15%) of the active ingredients to the smoking tobacco material. I have further found that satisfactory results are obtained if the proportions by weight of the sum total of mixture of 1-ethoxy-1-ethanol acetate and acetaldehyde used to flavoring material is between 0.05:1 and 0.50:1.

Any convenient method for incorporating the mixtures of 1-ethoxy-1-ethanol acetate and acetaldehyde in the tobacco product may be employed. Thus, the mixtures of 1-ethoxy-1-ethanol acetate and acetaldehyde taken alone or together with other flavoring additives may be dissolved in a suitable solvent such as food grade ethanol, pentane, diethyl ether and/or other volatile organic solvents, and the resulting solution may either be sprayed on the cured, cased and blended tobacco material; or the tobacco material or filter may be dipped into such solution. Under certain circumstances, a solution of the mixture of 1-ethoxy-1-ethanol acetate and acetaldehyde taken alone or further together with other flavoring additives as set forth above, may be applied by means of a suitable applicator such as a brush or roller on the paper or leaf wrapper for the smoking tobacco product, or it may be applied to the filter by either spraying or dipping or coating.

Further, it will be apparent that only a portion of the tobacco or substitute therefor need be treated and the thus treated tobacco may be blended with other tobacco before the ultimate tobacco product is formed. In such cases, the tobacco treated may have the mixtures of 1-ethoxy-1-ethanol acetate and acetaldehyde of my invention in excess of the amounts or concentrations above indicated so that when blended with other tobaccos, the final product will have the percentage within the indicated range.

While my invention is particularly useful in the manufacture of smoking tobacco such as cigarette tobacco, cigar tobacco and pipe tobacco, other tobacco products formed from sheeted tobacco dust or fines may also be used. As stated supra, the mixtures of 1-ethoxy-1-ethanol acetate and acetaldehyde of my invention can be incorporated with materials such as filter tip materials, seam paste, packaging materials and the like which are used along with the tobacco to form a product adapted for smoking. Furthermore, the mixtures of 1-ethoxy-1-ethanol acetate and acetaldehyde of my invention can be added to certain tobacco substitutes of natural or synthetic origin (e.g., dried lettuce leaves) and, accordingly, by the term "tobacco" as used throughout this specification is meant any composition intended for human consumption, by smoking or otherwise, whether composed of tobacco plant parts or substitute materials, or both.

It will thus be apparent that the mixtures of 1-ethoxy-1-ethanol acetate and acetaldehyde of my invention can be utilized to alter, modify, augment or enhance sensory properties, particularly organoleptic properties, such as flavor(s) and/or fragrance(s) of a wide variety of consumable materials.

The following examples serve to illustrate my invention, and this invention is to be considered restricted thereto only as indicated in the appended claims.

All parts and percentages given herein are by weight unless otherwise specified.

EXAMPLE I

PREPARATION OF 1-ETHOXY-1-ETHANOL ACETATE

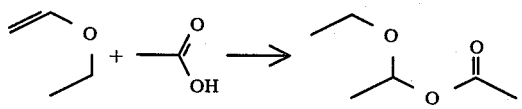

Into a 500 ml reaction flask, equipped with stirrer, cooling bath, thermometer, addition funnel and nitrogen blanket apparatus, is added 60 ml of acetic acid (1.1 moles) and 0.1 ml of acetyl chloride. Dropwise over a period of one hour, while maintaining the reaction mass at 30° C., is added 100 ml (1.0 moles) of ethyl vinyl ether. At the end of the addition of said ethyl vinyl ether, the reaction mass is stirred for a period of twelve hours, while maintaining the temperature thereof at 30° C.

The reaction mass is then distilled through a microdistillation apparatus, yielding the following fractions:

| Fraction No. | Vapor Temp. (°C.) | Liquid Temp. (°C.) | mm/Hg Pressure |
|---|---|---|---|
| 1 | 87/99 | 115/115 | Atmospheric |
| 2 | 100 | 115 | " |
| 3 | 100 | 115 | " |
| 4 | 101 | 117 | " |
| 5 | 102 | 123 | " |
| 6 | 102 | 123 | " |
| 7 | 70 | 170 | " |

FIG. 1 is the NMR spectrum for 1-ethoxy-1-ethanol acetate produced above.

FIG. 2 is the infra-red spectrum for 1-ethoxy-1-ethanol acetate produced above.

The NMR and the infra-red spectra, confirm that the structure of 1-ethoxy-1-ethanol acetate is:

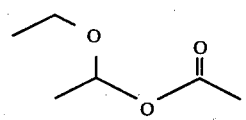

EXAMPLE II(A)

500 mg. of beta-cyclic dextrin is dissolved in 40 ml of water to which there is added a drop of 0.1 M sodium hydroxide solution to avoid having water with an acid pH. 0.3 ml of a solution containing 50 parts by weight of 1-ethoxy-1-ethanol acetate (prepared according to Example I) and 50 parts by weight of acetaldehyde is then added to the solution. The container for the solution is immediately stoppered and shaken vigorously to obtain a homogeneous solution. Then another solution is prepared by dissolving 1.0 grams of alpha-cyclic dextrin in 40 ml of water to which has been added one drop of 0.1 M sodium hydroxide solution. A 50:50 (weight:weight) mixture of 1-ethoxy-1-ethanol acetate and acetaldehyde in an amount of 0.5 ml is then dded to the resulting solution and the container is stoppered and shaken vigorously to obtain a homogeneous solution. Both solutions are then frozen and lyophilized overnight, to produce, respectively, beta-cyclic dextrin-1-ethoxy-1-ethanol acetate-acetaldehyde and alpha-cyclic dextrin-1-ethoxy-1-ethanol acetate-acetaldehyde complexes in dry form. These are analyzed colorimetrically using 10 mg of each complex per 100 ml of water and each complex is found to have bound 12% by weight of 50:50 1-ethoxy-1-ethanol acetate:acetaldehyde. A second analysis using 30 mg of complex per 100 ml of water shows the beta-cyclic dextrin complex to have 10.8% by weight of 50:50 acetaldehyde:1-ethoxy-1-ethanol acetate and the alpha-cyclic dextrin complex to have 11.4% of 50:50 1-ethoxy-1-lethanol acetate:acetaldehyde. The colorimetric analysis is run in the following way: to 1 ml of aqueous sample solution containing 0.1 mg (or 0.01% by weight) of dissolved complex, there is added 1.0 ml of a saturated alcoholic solution of 2,4-dinitrophenylhydrazine and one drop of concentrated hydrochloric acid, the resulting solution is mixed and then heated for 30 minutes at 50° C. After heating 10.0 ml of 10% potassium hydroxide in 70% alcohol is added, and the color is read at 480 millimicrons on a spectrophotometer. The concentration is read off a previously prepared color concentration curve. The foregoing assay is based on the method described by Snell, et al in "Colorimetric Method of Analyses", Vol. 3, page 253, D. Van Nostrand Co., Inc., New York 1953.

EXAMPLE II(B)

About 2.5 mg of the beta-cyclic dextrin complex of Example IIA is added to 6.7 gm of a dry orange-flavored beverage mix comprising sucrose, citric acid and a cloud-forming agent. When the mix is dissolved in about 50 ml of water, the beverage has the characteristic odor and flavor of fresh oranges, and is judged to be superior in these respects over a beverage prepared in exactly the same way but in which the complex is omitted.

EXAMPLE II(C)

500 mg. of beta-cyclic dextrin is dissolved in 40 ml of water to which there is added a drop of 0.1 M sodium hydroxide solution to avoid having water with an acid pH. 0.3 ml of a solution containing 2 parts by weight of 1-ethoxy-1-ethanol acetate (prepared according to Example I) and 98 parts by weight of acetaldehyde is then added to the solution. The container for the solution is immediately stoppered and shaken vigorously to obtain a homogeneous solution. Then another solution is prepared by dissolving 1.0 g of alpha-cyclic dextrin in 40 ml of water to which has been added one drop of 0.1 M sodium hydroxide solution. A 5:95 (weight:weight) mixture of 1-ethoxy-1-ethanol acetate:acetaldehyde in an amount of 0.5 ml is then added to the resulting solution and the container is stoppered and shaken vigorously to obtain a homogeneous solution. Both solutions are then frozen and lyophilized overnight to produce, respectively, beta-cyclic dextrin-1-ethoxy-1-ethanol acetate-acetaldehyde and alpha-cyclic destrin-1-ethoxy-1-ethanol acetate-acetaldehyde complexes in dry form. These are analyzed colorimetrically using 10 mg of each complex per 100 ml of water, and each complex is found to have bound 12% by weight of 5:95 1-ethoxy-1-ethanol acetate:acetaldehyde. A second analysis using 30 mg of complex per 100 ml of water shows the beta-cyclic dextrin complex to have 10.8% by weight of 5:95 1-ethoxy-1-ethanol acetate:acetaldehyde and the alpha-cyclic dextrin complex to have 11.4% of 5:95 1-ethoxy-1-ethanol acetate:acetaldehyde. The colorimetric analysis is run in the following way: To 1 ml of aqueous sample solution containing 0.1 mg (or 0.01% by weight) of dissolved complex, there is added 1.0 ml of a saturated alcoholic solution of 2,4-dinitrophenylhydrazine and one drop of concentrated hydrochloric acid, the resulting solution is mixed, and then heated for 30 minutes at 50° C. After heating 10.0 ml of 10% potassium hydroxide in 70% alcohol is added, and the color is read at 480 millimicrons on a spectrophotometer. The concentration is read off a previously prepared color concentration curve. The foregoing assay is based on the method described by Snell, et al in "Colorimetric Method of Analyses", Vol. 3, page 253, D. Van Nostrand Co., Inc. New York 1953.

EXAMPLE II(D)

About 2.5 mg of the beta-cyclic dextrin complex of Example II(C) is added to 6.7 gm of a dry orange flavored beverage mix comprising sucrose, citric acid and a cloud-forming agent. When the mix is dissolved in about 50 ml of water, the beverage has the characteristic odor and flavor of fresh oranges, and is judged to be superior in these respects over a beverage prepared in exactly the same way but in which the complex is omitted.

EXAMPLE III

ORANGE FLAVOR FORMULATION

An orange flavor formulation is prepared by admixing:

| Ingredients | Parts by Weight | |
|---|---|---|
| | III(A) | III(B) |
| Natural orange oil | 13.00 | 13.00 |
| A 50:50 mixture of 1-ethoxy-1-ethanol acetate:acetaldehyde | 1.58 | 0 |
| A 5:95 mixture of 1-ethoxy-1-ethanol acetate:acetaldehyde | 0 | 1.58 |
| Ethyl acetate | 0.10 | 0.10 |
| Ethyl butyrate | 0.50 | 0.50 |
| n-Propanol | 0.10 | 0.10 |
| trans-2-hexenal | 0.10 | 0.10 |
| Ethyl alcohol (95% food grade) | 60.00 | 60.00 |
| Fusel oil | 0.05 | 0.05 |
| Propylene glycol | 24.65 | 24.65 |

EXAMPLE III(A)

This flavor is denominated as Flavor "A". A second formulation, Flavor "B" is prepared by adding 2-ethylidene-cis-3-hexenal (1% in food grade ethanol) to a portion of Flavor "A" in the ratio of 2 parts to 100 parts of Flavor "A". To a third formulation denominated as Flavor "C", the 50:50 mixture of 1-ethoxy-1-ethanol acetate:acetaldehyde is substituted by acetaldehyde. To a fourth formulation denominated as "D", the mixture of 50:50 1-ethoxy-1-ethanol acetate:acetaldehyde is substituted with acetaldehyde and 2-ethylidene-cis-3-hexenal (1% in food grade ethanol) is added to it.

Each of Flavors "A", "B", "C" and "D" is added in the amount of 2 ounces per gallon of 32° Baume sugar syrup to produce a syrup for combination with water to form a drink. The beverage prepared using Flavors "A" and "B" are passable orange beverages of good character, flavor and intensity, whereas the flavors using "C" and "D" are not passable. The flavor prepared using "A" and "B" have a much improved flavor, particularly the flavor denominated as "B". The improvement contributed by the 50:50 mixture of 1-ethoxy-1-ethanol acetate:acetaldehyde (versus the acetaldehyde itself) is due to a much longer-lasting degree of freshness. The improvement contributed by the ethylidene hexenal is due to:

1. a greater degree of the natural character of freshly squeezed orange juice
2. an increase in the pulp-like notes
3. greater orange juice flavor depth.

The combination of 50:50 mixture of 1-ethoxy-1-ethanol acetate:acetaldehyde and the ethylidene hexenal gives rise to a highly unexpected, fresh, freshly squeezed orange juice flavor.

EXAMPLE III(B)

This flavor is denominated as Flavor "$A_1$". A second flavor formulation "$B_1$" is prepared by adding 2-ethylidene-cis-3-hexenal (1% in food grade ethanol) to a portion of Flavor "$A_1$" in the ratio of 2 parts to 100 parts of Flavor "$A_1$". To a third formulation denominated as Flavor "$C_1$", the 5:95 mixture of 1-ethoxy-1-ethanol acetate:acetaldehyde is substituted by acetaldehyde. To a fourth formulation denominated as "$D_1$", the mixture of 5:95 1-ethoxy-1-ethanol acetate: acetaldehyde is substituted with acetaldehyde and 2-ethylidene-cis-3-hexenal (1% in food grade ethanol) is added to it.

Each of Flavors "$A_1$", "$B_1$", "$C_1$" and "$D_1$" is added in the amount of 2 ounces per gallon of 32° Baume sugar syrup to produce a syrup for combination with water to form a drink. The beverage prepared using Flavors "$A_1$" and "$B_1$" are passable orange beverages of good character, flavor and intensity, whereas the flavors using "$C_1$" and "$D_1$" are not passable. The flavor prepared using "$A_1$" and "$B_1$" have a much improved flavored, particularly the flavor denominated as "$B_1$". The improvement contributed by the 5:95 mixture of 1-ethoxy-1-ethanol acetate:acetaldehyde (versus the acetaldehyde itself) is due to a much longer-lasting degree of freshness. The improvement contributed by the ethylidene hexenal is due to:

1. a greater degree of the natural character of freshly squeezed orange juice
2. an increase in the pulp-like notes
3. greater orange juice flavor depth.

The combination of 5:95 mixture of 1-ethoxy-1-ethanol acetate:acetaldehyde and the ethylidene hexenal gives rise to a highly unexpected, fresh, freshly squeezed, orange juice flavor.

EXAMPLE IV

APPLE FLAVOR FORMULATION

The following basic apple flavor formulation is prepared:

| Ingredients | Parts by Weight |
| --- | --- |
| Amyl acetate | 1.0 |
| Gamma decalactone | 1.5 |
| Caproic acid | 1.5 |
| n-Hexyl acetate | 2.5 |
| Coriander Oil | 0.5 |
| n-Hexyl iso-butyrate | 2.5 |
| n-Hexanal | 5.0 |
| Ethyl isovalerate | 5.0 |
| cis-3-Hexenol | 18.0 |
| Ethyl-2-methyl butyrate | 18.0 |
| trans-2-Hexenal | 18.0 |
| Apple Fusel Oil | 26.0 |
| Maltol | 0.5 |
| 95% food grade ethanol | 100.0 |

This basic apple flavor is compared in water with and without the addition of (a) the mixture of 50:50 1-ethoxy-1-ethanol acetate:acetaldehyde and (b) the mixture of 5:95 1-ethoxy-1-ethanol acetate:acetaldehyde, at the rate of 6 ppm and at the rate of 10 ppm in water. The flavor with the addition of the mixtures of 1-ethoxy-1-ethanol acetate and acetaldehyde have a fresh apple juice character with light fruity top notes. Both notes are missing in the flavor that does not contain the 1-ethoxy-1-ethanol acetate:acetaldehyde mixtures. For this reason, the flavors with the 1-ethoxy-1-ethanol acetate:acetaldehyde mixtures are preferred unanimously by three member bench panels.

In addition, 4 ppm of acetaldehyde are added to the basic apple flavor and compared with the flavors with mixtures of 1-ethoxy-1-ethanol acetate and acetaldehyde. Both flavors do have the fresh apple juice character and light, fruity top notes. But 1-ethoxy-1-ethanol acetate produces an even fresher character than just using plain acetaldehyde and this is unexpected, unobvious and advantageous insofar as 1-ethoxy-1-ethanol acetate is concerned.

EXAMPLE V

APPLE FLAVOR FORMULATION

A. POWDER FLAVOR FORMULATION 20 g of the flavor formulation of Example IV is emulsified in a solution containing 300 g gum acacia and 700 g water. The emulsion is spray-dried with a Bowen Lab Model Drier utilizing 260 c.f.m. of air with an inlet temperature of 500° F., an outlet temperature of 200° F. and a wheel speed of 50,000 rpm.

B. SUSTAINED RELEASE FLAVOR

The following mixture is prepared:

| Ingredients | Parts by Weight |
| --- | --- |
| Liquid apple flavors of Examples IV(A) and IV(B) | 20 |
| Propylene Glycol | 9 |
| Cab-O-Sil ® M-5 Brand of Silica produced by the Cabot corporation of 125 High Street, Boston, Mass. 02110; Physical Properties: Surface Area: 200 $m^2$/gm Nominal particle size: 0.012 microns Density: 2.3 lbs/cu. ft. | 5.00 |

The Cab-O-Sil ® is dispersed in each of the liquid apple flavor compositions of Example IV with vigorous stirring, thereby resulting in a viscous liquid. 71 parts by weight of the powder flavor composition of Part A, supra, is then blended into the said viscous liquid, with stirring, at 25° C. for a period of 30 minutes, resulting in a dry, free-flowing sustained release powder.

EXAMPLE VI 10 parts by weight of 50 Bloom pigskin gelatin is added to 90 parts by weight of water at a temperature of 150° F. The mixture is agitated until the gelatin is completely dissolved and the solution is cooled to 120° F. 20 parts by weight of each of the liquid apple flavor compositions of Example IV is added individually to solutions which are then homogenized to form an emulsion having a particle size typically in the range of 2–5 microns. The material is kept at 120° F. under which conditions the gelatin will not jell.

Coacervation is induced by adding slowly and uniformly, 40 parts by weight of a 20% aqueous solution of sodium sulphate. During coacervation the gelatin molecules are deposited uniformly about each oil droplet as a nucleus.

Gelation is effected by pouring the heated coacervate mixture into 1,000 parts by weight of 7% aqueous solution of sodium sulphate at 65° F. The resulting jelled coacervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE VII

CHEWING GUM 100 parts by weight of chicle are mixed with 4 parts by weight of each of the flavors prepared in accordance with Example V. 300 parts of sucrose and 100 parts of corn syrup are added. Mixing is effected in a ribbon blender with jacketed walls of the type manufactured by the Baker Perkins Co.

The resultant chewing gum blends are then manufactured into strips 1 inch in width and 0.1 inches in thickness. The strips are cut into lengths of 3 inches each. On chewing, the chewing gum has a pleasant, long-lasting apple flavor.

EXAMPLE VIII

CHEWING GUM 100 parts by weight of chicle are mixed with 18 parts by weight of the flavors prepared in accordance with Example VI. 300 parts of sucrose and 100 parts of corn syrup are then added. Mixing is effected in a ribbon blender with jacketed walls of the type manufactured by the Baker Perkins Co.

The resultant chewing gum blends are then manufactured into strips 1 inch in width and 0.1 inches in thickness. The strips are cut into lengths of 3 inches each. On chewing, the chewing gum has a pleasant, long-lasting apple flavor.

EXAMPLE IX

TOOTHPASTE FORMULATION

The following flavor formulations are prepared:
A. POWDER FLAVOR FORMULATION 20 grams of the flavor formulation of Example III(A) is emulsified in a solution containing 300 grams gum acacia and 700 grams water. The emulsion is spray dried with a Bowen Lab Model Drier utilizing 260 c.f.m. of air with an inlet temperature of 500° F. an outlet temperature of 200° F. and a wheel speed of 50,000 rpm.
B. SUSTAINED RELEASE FLAVOR The following mixture is prepared:

| Ingredients | Parts by Weight |
|---|---|
| Liquid orange flavor of Example III(A) | 15 |
| Propylene glycol | 9 |
| Ethyl cellulose | 4 |
| Xanthan gum | 4 |

The ethyl cellulose and xanthan gum are admixed. The resulting mixture is dispersed in the orange flavor composition of Example III(A) with vigorous stirring thereby resulting in a viscous liquid. 71 parts by weight of the powder flavor of Part A, supra, is then blended into the said viscous liquid with stirring at 25° C. for a period of 30 minutes resulting in a dry, free-flowing sustained release orange flavor powder.

The following separate groups of ingredients are prepared:

| Parts by Weight | Ingredient |
|---|---|
| Group "A" | |
| 30.200 | Glycerine |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |

-continued

| Parts by Weight | Ingredient |
|---|---|
| 2.000 | Sodium N-Lauroyl Sarcosinate (foaming agent) |
| Group "D" | |
| 1.200 | Flavor Material of this Example |
| 100.00 Total | |

PROCEDURE

1. The ingredients in Group "A" are stirred and heated in a steam jacketed kettle to 160° F.
2. Stirring is continued for an additional three to five minutes to form a homogeneous gel
3. The powders of Group "B" are added to the gel, while mixing, until a homogeneous paste is formed
4. With stirring, the flavor of "D" is added and lastly the sodium-n-lauroyl sarcosinate
5. The resultant slurry is then blended for one hour. The completed paste is then transferred to a three roller mill and then homogenized, and finally tubed.

The resulting toothpaste, when used in a normal toothbrushing procedure yields a pleasant orange flavor, of constant strong intensity throughout said procedure (1–1.5 minutes).

EXAMPLE X

CHEWABLE VITAMIN TABLETS

The flavor material produced according to the process of paragraph 1 of Example IX is added to a chewable vitamin tablet formulation at a rate of 10 gm/kg, which chewable vitamin tablet formulation is prepared as follows:

In a Hobart Mixer, the following materials are blended to homogeneity:

| Ingredients | Gms/1000 Tablets |
|---|---|
| Vitamin C (ascorbid acid) as ascorbic acid-sodium ascorbate mixture 1:1 | 70.11 |
| Vitamin B$_1$ (thiamine mononitrate) as Rocoat ® thiamine mononitrate 33⅓% (Hoffman La Roche) | 4.0 |
| Vitamin B$_2$ (riboflavin) as Rocoat ® riboflavin 33⅓% | 5.0 |
| Vitamin B$_6$ (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin B$_{12}$ (cyanocobalamin) as Merck 0.1% in gelatin | 3.5 |
| Vitamin E (dl-alpha tocopheryl acetate) as dry Vitamin E acetate 33⅓% | 6.6 |
| d-Biotin | 0.044 |
| Flavor of Example IX | (as indicated above) |
| Certified lake color | 5.0 |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong orange flavor for a period of 12 minutes.

EXAMPLE XI

CHEWING TOBACCO

Onto 100 pounds of tobacco for chewing (85% Wisconsin leaf and 15% Pennsylvania leaf) the following casing is sprayed at the rate of 30%.

| Ingredients | Parts by Weight |
|---|---|
| Corn syrup | 60 |
| Licorice | 10 |
| Glycerine | 20 |
| Fig Juice | 4.6 |
| Prune Juice | 5 |
| 50:50 mixture of 1-ethoxy-1-ethanol acetate and acetaldehyde | 0.04 |

The resultant product is redried to a moisture content of 20%. On chewing, this tobacco has an excellent substantially consistent, long-lasting apple-like nuance, in conjunction with the tobacco notes.

EXAMPLE XII

A tobacco blend is made up by mixing the following materials:

| Ingredient | Parts by Weight |
|---|---|
| Ethyl butyrate | .05 |
| Ethyl vaterate | .05 |
| Maltol | 2.00 |
| Cocoa extract | 26.00 |
| Coffee extract | 10.00 |
| Ethyl alcohol | 20.00 |
| Water | 41.90 |

The above flavor is incorporated into model "filter" cigarettes at the rate of 0.1%. One-third of these model filter cigarettes are treated in the tobacco section with a 50:50 mixture of 1-ethoxy-1-ethanol acetate (produced according to Example I): acetaldehyde at 100 ppm per cigarette. Another one-third of these model cigarettes is treated in the filter with a 50:50 mixture of 1-ethoxy-1-ethanol acetate (produced according to Example I): acetaldehyde at the rate of $2 \times 10^{-5}$ gm. When evaluated by paired comparison, the cigarettes treated both in the tobacco and in the filter with the 1-ethoxy-1-ethanol acetate are found, in smoke flavor, to be more tobacco-like, with enhanced sweet, fruity, winey and fresh berry nuances. When replacing the mixture of 1-ethoxy-1-ethanol acetate and acetaldehyde with acetaldehyde, the flavor is much weaker and the amount of freshness and "lift" to the smoke is much less. 1-ethoxy-1-ethanol acetate gives an intense freshness and lift to smoke when compared to cigarettes either without anything added or with acetaldehyde added in the same ratio.

EXAMPLE XIII

The following perfume formulations are prepared:

| | Parts by Weight | |
| Ingredients | XIII(A) | XIII(B) |
|---|---|---|
| Geranium bourbon | 175 | 175 |
| Citronellol | 150 | 150 |
| Geraniol | 100 | 100 |
| Phenyl ethyl alcohol | 90 | 90 |
| Amyl cinnamic aldehyde | 200 | 200 |
| Cyclamal | 20 | 20 |
| Lyral[1] | 100 | 100 |
| Tetrahydro linalool | 37.5 | 37.5 |
| Citronellyl acetate | 125 | 125 |
| Phenyl ethyl acetate | 5 | 5 |
| Phenyl acetaldehyde dimethyl acetal | 10 | 10 |
| Cinnamic alcohol | 35 | 35 |
| Terpineol | 100 | 100 |
| Linalyl acetate | 25 | 25 |
| Musk ketone | 10 | 10 |
| Indole | 10 | 10 |
| Geranyl nitrile | 10 | 10 |
| 7-methyl-3-methylene-6-octenenitrile | 10 | 10 |
| A 50:50 mixture of 1-ethoxy-1-ethanol acetate:acetaldehyde | 25 | 0 |
| A mixture of 5:95 1-ethoxy-1-ethanol acetate:acetaldehyde | 0 | 25 |

[1]Lyral is the registered trademark of International Flavors and Fragrances, Inc., for 4-(4-methyl, 4-hydroxy amyl)-Δ-3-cyclohexene carboxaldehyde.

The addition of the mixtures of 1-ethoxy-1-ethanol acetate and acetaldehyde to the foregoing formulations, which are lemon fragrances, impart a freshness to the lemon fragrances causing them to be more natural-like in aroma and, in addition, causing them to be longer-lasting in aroma and in intensity.

EXAMPLE XIV

PREPARATION OF A COSMETIC POWDER COMPOSITION

Cosmetic powders are prepared by mixing in a ball mill 100 g of talcum powder with 0.25 grams of the perfume composition prepared according to either of Examples XIII(A) or XIII(B). Each has an excellent fresh, lemony aroma. The "fresh" aroma nuance is imparted to this cosmetic powder as a result of the use of mixtures of 1-ethoxy-1-ethanol acetate and acetaldehyde.

EXAMPLE XV

PERFUMED LIQUID DETERGENT

Concentrated liquid detergent (Lysine salt of n-dodecylbenzene sulfonic acid, as more specifically described in U.S. Pat. No. 3,948,818 issued on Apr. 6, 1976) with fresh, lemony aroma nuances are prepared containing 0.10%, 0.15% and 0.20% of the fragrance prepared according to each of Examples XIII(A) and XIII(B). They are prepared by adding and homogeneously mixing the appropriate quantity of fragrance formulation prepared according to each of Examples XIII(A) and XIII(B) in the liquid detergent. The detergents all possess excellent fresh, lemony aromas, the intensity increasing with greater concentrations of perfume compositions of Examples XIII(A) and XIII(B). This "fresh" aroma is contributed by the 1-ethoxy-1-ethanol acetate produced according to Example I.

EXAMPLE XVI

PREPARATION OF A COLOGNE AND HANDKERCHIEF PERFUME

The compositions prepared according to each of Examples XIII(A) and XIII(B) are individually incorporated into a cologne at concentrations of 2.0%, 2.5%, 3.0%, 3.5%, 4.0%, 4.5% and 5.0% in 85%, 90% and 95% aqueous food grade ethanol solutions, and into handkerchief perfume at concentrations of 15%, 20%, 25% and 30% (in 85%, 90% and 95% aqueous food grade ethanol solutions). Distinctive and definitive fresh lemony aromas are imparted to the cologne and to the handkerchief perfume at all levels indicated above. The "fresh" aroma nuance is contributed by the 1-ethoxy-1-ethanol acetate produced according to Example I.

EXAMPLE XVII

PREPARATION OF SOAP COMPOSITION

One hundred grams of soap chips (IVORY ®, registered trademark of the Procter & Gamble Co. of Cincinnati, Ohio) are mixed individually with one gram of each of the formulations of Examples XIII(A) and XIII(B) until a homogeneous composition is obtained. The homogeneous composition is then treated under three atmospheres pressure at 180° C. for a period of three hours and the resulting liquid is placed into a soap mold. The resulting soap cakes, on cooling, manifest excellent fresh, lemony aromas with the "fresh" nuance being contributed by the 1-ethoxy-1-ethanol acetate produced according to Example I.

EXAMPLE XVIII

PREPARATION OF A SOLID DETERGENT COMPOSITION

A detergent is prepared from the following ingredients according to Example I of Canadian Pat. No. 1,007,948:

| Ingredients | Percent by Weight |
| --- | --- |
| "Neodol 45-II" (a $C_{14}$—$C_{15}$ alcohol ethoxylated with 11 moles of ethylene oxide | 12 |
| Sodium carbonate | 55 |
| Sodium citrate | 20 |
| Sodium sulfate, water brighteners | q.s. |

This detergent is a "phosphate-free" detergent. A total of 100 grams of this detergent is admixed separately with 0.15 grams of each of the perfume formulations of Example XIII(A) and XIII(B). The detergent samples have excellent fresh, lemony aromas. The "fresh" nuance is imparted as a result of the use of 1-ethoxy-1-ethanol acetate produced according to Example I.

EXAMPLE XIX

Utilizing the procedure of Example I of column 15 of U.S. Pat. No. 3,632,396, a nonwoven cloth substrate useful as a dryer-added fabric softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
57 percent $C_{20-22}$ HAPS
22 percent isopropyl alcohol
20 percent antistatic agent
1 percent of one of the perfume compositions of Examples XIII(A) or XIII(B) (which give rise to a fresh lemony aroma) (the fresh nuance is contributed by the 1-ethoxy-1-ethanol acetate produced according to Example I)

A fabric softening composition prepared as set forth above having the above aroma chracteristics, essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of substrate. The aroma set forth above is imparted in a pleasant manner to the headspace in the dryer on operation thereof, using said dryer-added, fabric softening non-woven fabric.

EXAMPLE XX

A completely frozen composition in particulate form and having the following formula:

| Ingredients | Percent |
| --- | --- |
| Water | 67 |
| Hydrolized cereal solids (MOR-REX) | 22 |
| 50:50 acetaldehyde:1-ethoxy-1-ethanol acetate mixture | 11 | is loaded into trays to a depth of approximately 0.6 to 0.8 cm. The frozen composition is thereafter freeze-dried for a period of 23 hours employing a shelf temperature of 50° F. and a condenser temperature of −40° F.

The temperature of the frozen product rises from −13° F. to −5° F. in approximately 1½ hours. At this point there is some evidence of melting as indicated by the shiny surfaces on the frozen particles; however, melting does not occur to an extent sufficient to impair acetaldehyde retention. After a total of 16 hours, product temperature rises to approximately 50° F. thereby equalling the shelf temperature. The product temperature is maintained at 50° F. for an additional 4 hours after which the shelf temperature is raised to 68° F. for 3 more hours thereby giving a total drying time of 23 hours. The moisture content of the final product is approximately 0.2%.

During the entire freeze-drying process, the pressure of the evacuated chamber is maintained at a value of approximately 150 microns.

The freeze-dried product thus obtained can be heated to temperatures on the order of 50°–60° F. under high vacuum conditions without significant loss of acetaldehyde or 1-ethoxy-1-ethanol acetate or E-A mixture. Moreover, acetaldehyde and 1-ethoxy-1-ethanol acetate retention is excellent despite open storage of the freeze-dried product for periods of time up to 90 days under room temperature conditions and a relative humidity of 50%.

The E-A mixture, hydrolyzed cereal solids, water composition is prepared for freeze-drying by initially forming a clear solution of the hydrolyzed cereal solids in water at a temperature within a range of 180°–190° F. and adding the E-A mixture thereto after cooling the clear solution to a temperature of 40° F. The solution thus obtained is converted to a completely frozen state by drop-feeding same into liquid nitrogen at a temperature of −320° F. whereupon it freezes substantially immediately, forming substantially spherical particles having an average particle size within the range of ¼ to ½ cm. The particles thus obtained are supplied to the freeze-drying apparatus for processing as described.

EXAMPLE XXI

A composition prepared and frozen as described in Example XX and having the following composition:

| Ingredients | Percent |
|---|---|
| Water | 30 |
| Hydrolyzed cereal solids (MOR-REX) | 50 |
| 5:95 weight:weight mixture of 1-ethoxy-1-ethanol acetate:acetaldehyde | 20 | is freeze-dried for a period of approximately 15 hours under a pressure ranging from about 100 to 300 microns of mercury, a shelf temperature within the range of 0° F. to 100° F., the product temperature being within the range of from −50° F. to 60° F. The condenser temperature is maintained at −60° F. The product is dried to a final moisture content of 0.2%.

Acetaldehyde, 1-ethoxy-1-ethanol acetate and E-A mixture retention in the freeze-dried product is thereafter evaluated by open storage of the composition at room temperature in a relative humidity of up to 50%. The results obtained are as follows:

TABLE I

| Days standing | 0 | 6 | 13 | 20 | 40 | 60 |
|---|---|---|---|---|---|---|
| Percent E-A mixture in the freeze-dried product | 15.2 | 13.7 | 13.1 | 12.5 | 11.7 | 11.5 |

As the foregoing results indicated, excellent acetaldehyde, 1-ethoxy-1-ethanol acetate and E-A mixture retention is obtained despite subjection of the freeze-dried product to open storage conditions for extended periods of time. As will further be noted, the percent E-A mixture in the product shows a leveling off effect for periods of standing exceeding 40 days.

EXAMPLE XXII

The following compositions are prepared:

| | Percent | |
|---|---|---|
| Ingredients | (a) | (b) |
| Water | 22.2 | 40 |
| Hydrolyzed cereal solids (MOR-REX) | 74 | 40 |
| 50:50 mixture of acetaldehyde:1-ethoxy-1-ethanol acetate | 3.8 | 20 |

Each of the above solutions is formed by dissolving the hydrolyzed cereal solids in water at a temperature of about 185° F., cooling the solution thus formed to a temperature of about 35°-40° F. and adding the indicated quantity of E-A mixture thereto. Each of said compositions is thereafter completely frozen by pouring same into stainless steel plates (36×17×2″) and cooling on a bed of dry ice; a completely frozen condition is obtained after about 5 hours.

The frozen material is ground in apparatus maintained at a temperature sufficiently low to insure against melting of the frozen product and thereafter placed in trays for insertion into the freeze-drying apparatus.

Freeze-drying is thereafter carried out in the manner described in Example XXI. E-A mixture retention studies conducted in the manner described in Example XXI yield the following results:

TABLE II

| Days Standing | Percent E-A Mixture in Freeze Dried Product | |
|---|---|---|
| | Composition (a) | Composition (b) |
| 0 | 17.7 | 13.9 |
| 6 | 17.7 | 14.3 |
| 39 | 12.9 | 13.1 |

Again, the results obtained indicate excellent E-A mixture retention under normal open storage conditions.

EXAMPLE XXIII

The following composition, prepared and frozen as described in Example XX and having the formula:

| Ingredient | Percent |
|---|---|
| Water | 66.7 |
| Hydrolyzed cereal solids (MOR-REX) | 22.2 |
| 5:95 weight:weight mixture of 1-ethoxy-1-ethanol acetate:acetaldehyde | 11.1 | is placed in dry ice-cooled, ribbed aluminum plates and freeze-dried employing a shelf temperature of about 50° F., a condenser temperature of −50° F. and a vacuum ranging from 150 to 200 microns of mercury. The freeze-drying was carried out for a period of 48 hours to a moisture content of 0.2%.

E-A mixture retention studies with the freeze-dried material thus obtained yields results similar to those described in the preceding examples.

EXAMPLE XXIV

To the following composition:

| Ingredient | Amount (grams) |
|---|---|
| Orange flavorant of Example III(A) and color | 0.95 |
| Citric acid | 20.0 |
| Dextrose | 39.35 |
| Sucrose | 1000 | is added 3.85 grams of freeze-dried E-A mixture-containing composition prepared as in the foregoing Example XX and containing 0.46 grams (12%) of E-A mixture to produce a non-carbonated orange beverage formulation. The formulation thus obtained is packaged in a paper envelope which is non-hermetically sealed and thus subject to moisture pick-up from the atmosphere.

What is claimed is:

1. A mixture of 1-ethoxy-1-ethanol acetate having the structure:

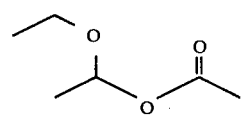

and acetaldehyde, the range of weight ratios of 1-ethoxy-1-ethanol acetate:acetaldehyde being from 50:50 down to 5:95.

2. A process for the preparation of a flavoring composition which comprises subliming water vapor from ice crystals by means of applying a vacuum to a frozen mixture comprising (a) from about 6 to 1 parts water; (b) from about 4 to 2 parts of an ingestibly acceptable non-hygroscopic carrier comprising a non-hygroscopic carbohydrate and (c) from about 2 to 1 parts of 1-ethoxy-1-ethanol acetate:acetaldehyde mixture the range of weight ratios of 1-ethoxy-1-ethanol acetate:acetaldehyde being from 50:50 down to 5:95 and obtaining a composition stably retaining at least 7% by weight of acetaldehyde:1-ethoxy-1-ethanol acetate mixture, based on the total weight of acetaldehyde:1-ethoxy-1-ethanol acetate mixture, said non-hygroscopic carbohydrate carrier, and water.

3. A process according to claim 2 wherein said frozen mixture is in particulate form.

4. A process according to claim 2 wherein said frozen mixture is in the form of a continuous sheet.

5. A process according to claim 2 wherein said carrier comprises hydrolyzed cereal solids.

6. A process according to claim 2 wherein said frozen mixture is prepared by freezing an aqueous mixture of said carrier and mixture of 1-ethoxy-1-ethanol acetate and acetaldehyde in liquid nitrogen.

7. A process according to claim 6 wherein said aqueous solution is prepared by first admixing said carrier with water at a temperature within the range of 180° F. to 212° F., cooling the mixture thus obtained to a temperature within the range of 35° C. to 45° C. and incorporating a mixture of acetaldehyde and 1-ethoxy-1-ethanol acetate in the cooled mixture.

8. A process according to claim 6 wherein said aqueous mixture is prepared by condensing a mixture of acetaldehyde and 1-ethoxy-1-ethanol acetate into an aqueous mixture of said carrier, the acetaldehyde and the 1-ethoxy-1-ethanol acetate being continually refluxed during said condensing.

9. A flavoring composition comprising an ingestibly acceptable carrier comprising a non-hygroscopic carbohydrate and a mixture of 1-ethoxy-1-ethanol acetate and acetaldehyde, the range of weight ratios of 1-ethoxy-1-ethanol acetate:acetaldehyde being from 50:50 down to 5:95, the acetaldehyde being present in excess of about 7% by weight based on the total weight of 1-ethoxy-1-ethanol acetate:acetaldehyde mixture, said carbohydrate and water.

10. A composition according to claim 9 wherein said carrier comprises hydrolyzed cereal solids.

11. A process for altering the flavor of a foodstuff which comprises incorporating in said foostuff a small but effective quantity of the composition of claim 9.

12. A process according to claim 11 wherein said carrier comprises hydrolyzed cereal solids.

13. A process for augmenting or enhancing the aroma or taste of a foodstuff comprising the step of adding to foodstuff from 0.05 parts per million up to about 500 parts per million based on the total composition of a mixture of 1-ethoxy-1-ethanol acetate having the structure:

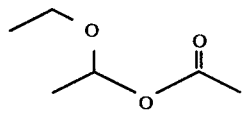

and acetaldehyde, the range of weight ratios of 1-ethoxy-1-ethanol acetate:acetaldehyde being from 50:50 down to 5:95.

14. A process for augmenting or enhancing the aroma or taste of a chewing gum comprising the step of adding to a chewing gum base from 0.05 ppm up to about 500 parts per million of a mixture of 1-ethoxy-1-ethanol acetate having the structure:

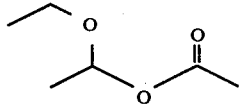

and acetaldehyde, the range of weight ratios of 1-ethoxy-1-ethanol acetate:acetaldehyde being from 50:50 down to 5:95.

15. The process of claim 13 where there is additionally added to the foodstuff 2-ethylidene-cis-3-hexenal.

* * * * *